(12) United States Patent
Kreszowski

(10) Patent No.: US 7,520,932 B2
(45) Date of Patent: Apr. 21, 2009

(54) METHOD OF ANALYZING CARBON CONCENTRATION IN CRYSTALLINE SILICON

(75) Inventor: Doug Kreszowski, Saginaw, MI (US)

(73) Assignee: Dow Corning Corporation, Midland, MI (US)

(*) Notice: Subject to any disclaimer, the term of this patent is extended or adjusted under 35 U.S.C. 154(b) by 20 days.

(21) Appl. No.: 11/693,238

(22) Filed: Mar. 29, 2007

(65) Prior Publication Data

US 2007/0238189 A1 Oct. 11, 2007

Related U.S. Application Data

(60) Provisional application No. 60/744,315, filed on Apr. 5, 2006.

(51) Int. Cl.
| | |
|---|---|
| *C30B 11/04* | (2006.01) |
| *C30B 17/00* | (2006.01) |
| *B01D 9/02* | (2006.01) |
| *G01N 33/00* | (2006.01) |

(52) U.S. Cl. ............................ 117/49; 23/301; 117/11; 117/61; 422/253; 436/72

(58) Field of Classification Search .................. 23/301; 117/49, 61; 422/253; 436/72
See application file for complete search history.

(56) References Cited

U.S. PATENT DOCUMENTS 5,108,720 A   4/1992  Bourbina et al.
5,361,128 A   11/1994 Bourbina et al.
5,436,164 A   7/1995  Dumler et al.
6,251,182 B1  6/2001  Luna et al.

OTHER PUBLICATIONS

Lydia L. Hwang et al, Measurement of Carbon Concentration in Polycrystalline Silicon Using FTIR, Journal of The Electro Chemical Society, vol. 138, No. 2, Feb. 1991, pp. 576-581.
ASTM Designation: F1723-02; Standard Practice for Evaluation of Polycrystalline Silicon Rods by Float-Zone Crystal Growth and Spectroscopy, ASTM International, West Conshohocken, PA, U.S., pp. 631-639.(2002).
ASTM Designation: F1391-93 (Reapproved 2000); Standard Test Method for Substitutional Atomic Carbon Content of Silicon by Infrared Absorption, ASTM International, West Conshohocken, PA, U.S., (1994), pp. 384-389.

*Primary Examiner*—Felisa C Hiteshew
(74) *Attorney, Agent, or Firm*—Howard & Howard Attorneys PLLC

(57) ABSTRACT

A method of analyzing carbon concentration in crystalline silicon includes providing a section from a zoned and annealed silicon core. The zoned and annealed core is extracted from a polycrystalline silicon composition and has a columnar shape. The zoned and annealed core includes a single crystalline silicon region and a freeze-out melt region. The freeze-out melt region is disposed adjacent to the single crystalline silicon region, and the regions are spaced along a length of the columnar shape. Specifically, the section is provided from the freeze-out melt region, with the entire freeze-out melt region in the section. A carbon concentration of the section is determined. By providing the section from the freeze-out melt region, as opposed to the polycrystalline silicon composition, determination of carbon concentration in the crystalline silicon is enabled with a sensitivity at less than or equal to 10 parts per billion atomic.

26 Claims, 1 Drawing Sheet

Carbon Concentration in Freeze-Out Melt Region * (weight of section/weight of single crystalline silicon region) (ppma)

METHOD OF ANALYZING CARBON CONCENTRATION IN CRYSTALLINE SILICON

RELATED APPLICATIONS

This patent application claims priority to and all advantages of U.S. Provisional Patent Application No. 60/744,315, which was filed on Apr. 5, 2006.

FIELD OF THE INVENTION

The present invention generally relates to a method of determining carbon concentration in crystalline silicon. More specifically, the invention relates to a method of determining carbon concentration in a section provided from a zoned and annealed silicon core that is extracted from a polycrystalline silicon composition and, optionally, determining carbon concentration in a single crystalline silicon region of the zoned and annealed silicon core, and optionally determining carbon concentration in the polycrystalline silicon composition.

BACKGROUND OF THE INVENTION

The fabrication of integrated circuits and other electronic components utilizes crystalline silicon, more specifically, single crystalline silicon, that possesses very high crystalline perfection. To control the quality of the single crystalline silicon, it is important to be able to determine the concentration of contaminates in polycrystalline silicon compositions from which the single crystalline silicon is formed.

One of the contaminates that affects the quality of the single crystalline silicon and that is typically analyzed through standard methods is carbon. A standard method of analyzing carbon concentration in crystalline silicon is set forth in ASTM F-1723-02. The crystalline silicon may be either polycrystalline silicon, single crystalline silicon, or a cross section of the single crystalline silicon, with different algorithms used to determine carbon concentration in the polycrystalline silicon and single crystalline silicon based on the carbon concentration in the cross section of the single crystalline silicon. A specific method of using infrared absorption to analyze carbon concentration in crystalline silicon is set forth in ASTM F 1391-93.

For the method of analyzing the carbon concentration in crystalline silicon, as set forth in ASTM F 1723-02, a polycrystalline silicon composition is provided. A polycrystalline silicon core, or ingot, is extracted from the polycrystalline silicon composition. The polycrystalline silicon core is then annealed at a temperature of 1360° C. for 2 hours. A 2 mm thick cross section is cut from the annealed polycrystalline silicon core. Carbon concentration in the 2 mm thick cross section is determined with a Fourier Transform infrared (FT-IR) spectrometer in accordance with ASTM F 1391-93. Based on the carbon concentration in the cross section, a bulk carbon concentration in the polycrystalline silicon composition may be determined based on well known algorithms.

Although current methods of analyzing carbon concentration in crystalline silicon provide useful results, the results are only sensitive to differences in carbon concentration of about 50 parts per billion atomic or greater. Certain cryogenic FT-IR analyses may be able to determine carbon concentration with greater sensitivity; however, the equipment required to perform cryogenic FT-IR analyses is expensive and requires precise environmental control to attain accurate results.

Due to the need for extremely pure crystalline silicon, and the need to determine the exact carbon concentration in crystalline silicon being used, it would be desirable to develop a new method of analyzing carbon concentration in the crystalline silicon with even greater sensitivity than 50 parts per billion atomic.

SUMMARY OF THE INVENTION AND ADVANTAGES

The subject invention provides a method of analyzing carbon concentration in crystalline silicon. For the method, a section is provided from a zoned and annealed silicon core. The zoned and annealed core is extracted from a polycrystalline silicon composition and has a columnar shape. The zoned and annealed core includes a single crystalline silicon region and a freeze-out melt region. The freeze-out melt region is disposed adjacent to the single crystalline silicon region, and the regions are spaced along a length of the columnar shape. Specifically, the section is provided from the freeze-out melt region, with the entire freeze-out melt region in the section. A carbon concentration of the section is determined. Optionally, carbon concentration of the zoned and annealed silicon core is determined based on the carbon concentration of the section, the weight of the section, a weight of the single crystalline silicon region, and an effective segregation coefficient. Also optionally, carbon concentration of the crystalline silicon composition is determined based on the carbon concentration of the zoned and annealed silicon core.

By providing the section from the freeze-out melt region, as opposed to the polycrystalline silicon composition, determination of carbon concentration in the crystalline silicon is enabled with a sensitivity at less than or equal to 10 parts per billion atomic. The determination of carbon concentration in the crystalline silicon with the sensitivity at less than or equal to 10 parts per billion atomic is due primarily to higher carbon concentration in the freeze-out melt region, as compared to carbon concentration in the polycrystalline silicon composition. As a result, immeasurable differences in carbon concentration in polycrystalline silicon cores are magnified and thus measurable between the freeze-out melt regions, thereby enabling the sensitivity at less than or equal to 10 parts per billion atomic in the determination of carbon concentration in the crystalline silicon.

BRIEF DESCRIPTION OF THE DRAWINGS

Other advantages of the present invention will be readily appreciated, as the same becomes better understood by reference to the following detailed description when considered in connection with the accompanying drawing wherein.

DETAILED DESCRIPTION OF THE PREFERRED EMBODIMENTS

Figure 1:
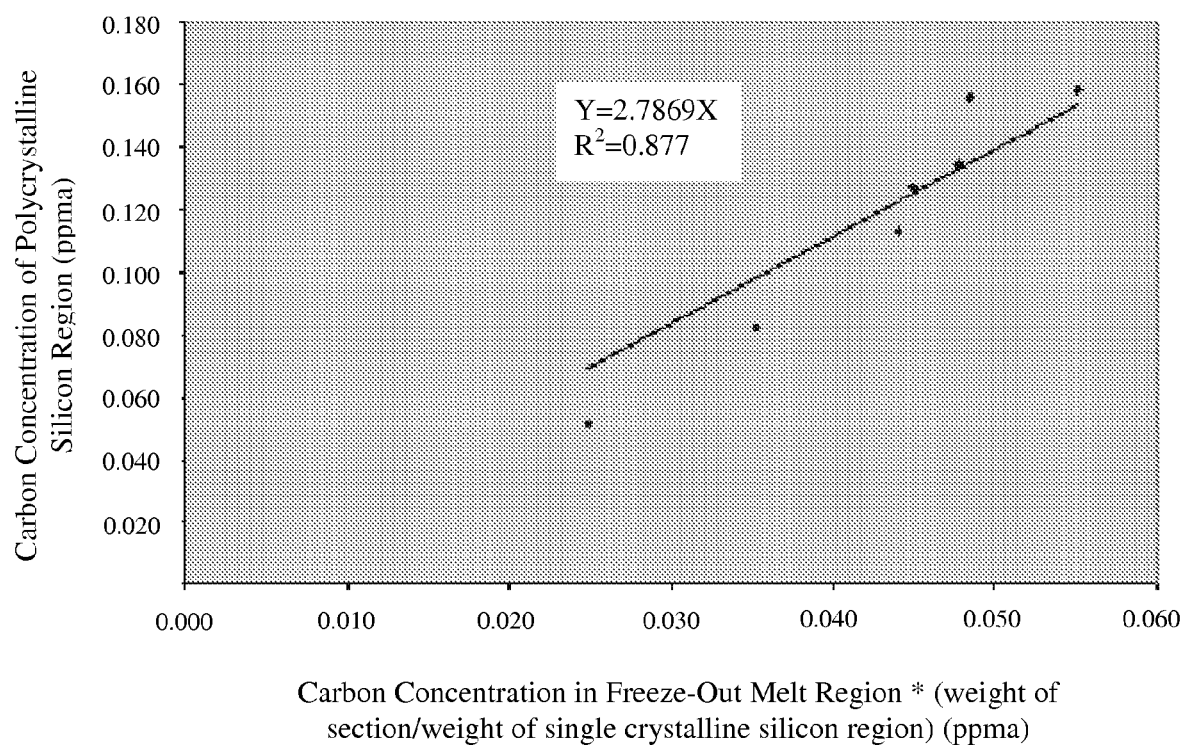
FIG. 1 is a graph showing a plot correlating carbon concentration in reference polycrystalline silicon compositions of known carbon concentration and carbon concentration in freeze-out melt regions of zoned and annealed silicon cores provided from the reference polycrystalline silicon composition with an inverse of a slope of the plot representing an effective segregation coefficient.

A method of the present invention includes analyzing carbon concentration in crystalline silicon. Crystalline silicon, more specifically single crystalline silicon, is used in the fabrication of integrated circuits and other electronic components such as rectifiers, transistors, phototransistors, and the like. Ideal single crystalline silicon for use in the integrated circuits and other electronic components has very high crystalline perfection, since defects in the crystalline silicon affect minority carrier lifetimes. The defects may occur at grain boundaries of grains in polycrystalline silicon compositions. To eliminate the grain boundaries, the polycrystalline silicon compositions are converted to single crystalline silicon through well known methods such as Czochralski (CZ) crystal growth or float zone (FZ) growth. Defects are also caused in the crystalline silicon due to the presence of contaminates such as carbon. The carbon may be naturally present in raw material, i.e., quartzite, from which the crystalline silicon is refined. Carbon concentration in the crystalline silicon is analyzed on a parts per million atomic basis. As such, harmful amounts of carbon may also be introduced into the crystalline silicon while forming the crystalline silicon, if not performed in an extremely clean environment.

Due to the effect that even miniscule amounts of carbon has on performance and quality of the crystalline silicon, it is important to be able to determine the carbon concentration in the crystalline silicon. For purposes of the present invention, it is to be appreciated that the crystalline silicon may be either a polycrystalline silicon composition, a single crystalline silicon region in a zoned and annealed silicon core that is extracted from the polycrystalline silicon composition, or a section provided from the zoned and annealed silicon core. Determination of carbon concentration in the polycrystalline silicon composition and the single crystalline silicon region of the zoned and annealed silicon core are optional, with only the determination of carbon concentration in the section necessary in order to analyze carbon concentration in the crystalline silicon for purposes of the present invention.

For the method of the present invention, the zoned and annealed silicon core from the polycrystalline silicon composition may be provided. Alternatively, the section from the zoned and annealed silicon core may be provided, to be described in further detail below. The section from the zoned and annealed silicon core is key to the analysis of carbon concentration in the crystalline silicon, regardless of whether or not a third party provides the section or the section is removed from the zoned and annealed silicon core at the same site as analysis of carbon concentration in the section. The zoned and annealed silicon core may be provided by a third party, or a polycrystalline silicon core may be extracted from the polycrystalline silicon composition, and the polycrystalline silicon core may be zoned and annealed to form the zoned and annealed silicon core at the same site as analysis of carbon concentration. Typically, due to the risk of contamination, the polycrystalline silicon core is extracted from the polycrystalline silicon composition, the polycrystalline silicon core zoned and annealed to form the zoned and annealed silicon core, and the section removed from the zoned and annealed silicon core, at the same site as analysis of carbon concentration.

The polycrystalline silicon composition may be formed through methods that are known in the art. More specifically, the polycrystalline silicon composition may be formed through chemical vapor deposition of silanes onto a heated silicon element, i.e., a filament, and typically has a columnar shape. However, it is to be appreciated that the polycrystalline silicon composition may be formed through any method known in the art. The polycrystalline silicon composition may be chopped and packaged for sending to other facilities, where single crystalline silicon may be formed from the chopped polycrystalline silicon composition. Prior to chopping and packaging the polycrystalline silicon composition, the polycrystalline silicon core is typically extracted from the polycrystalline silicon composition in order to analyze the carbon concentration in the polycrystalline silicon composition. However, it is to be appreciated that the carbon concentration in the polycrystalline silicon composition may be analyzed after chopping and packaging.

The polycrystalline silicon core may be extracted from the polycrystalline silicon composition through any suitable method, and may be extracted either perpendicular or parallel to the columnar shape of the polycrystalline silicon composition. Typically, the polycrystalline silicon core is extracted from the polycrystalline silicon composition with a diamond core drill using a drill press. The polycrystalline silicon core may have a diameter of from about 15 to about 25 mm, typically about 19 mm. The polycrystalline silicon core may have a length of from about 50 to about 120 mm, typically about 90 mm. The exact diameter and length of the polycrystalline silicon core is unimportant, so long as the polycrystalline silicon core can fit within a float-zone crystal-growth apparatus that is used to zone the polycrystalline silicon core.

After the polycrystalline silicon core is extracted from the polycrystalline silicon composition, the polycrystalline silicon core is typically degreased using a suitable solvent, such as ozone, to remove any surface carbon contamination. The polycrystalline silicon core may then be etched in acid. The acid is typically a solution of nitric acid and hydrofluoric acid. The polycrystalline silicon core is typically placed into a clean etch boat including the acid and etched for a sufficient amount of time to remove about 100 μm from a surface of the polycrystalline silicon core in order to remove contaminates that may be present after extracting the polycrystalline silicon core. Methods of etching the polycrystalline silicon core are known in the art and are specifically described in ASTM F 1723-03.

The polycrystalline silicon core is zoned to form a zoned silicon core. It is to be appreciated that, while the polycrystalline silicon core is zoned at some point to form the zoned silicon core, the step of zoning is not explicitly required for the method of the present invention. For example, a pre-zoned silicon core may be provided from a third party. As alluded to above, the polycrystalline silicon core is float-zoned in the float-zone crystal-growth apparatus. Specific methods for float zoning the polycrystalline silicon core are known in the art and described in detail in ASTM F 1723-03. The resulting zoned silicon core has a columnar shape and includes the single crystalline silicon region and a freeze-out melt region. The freeze-out melt region is disposed adjacent to the single crystalline silicon region, and the regions are spaced along a length of the columnar shape.

Typically, the single crystalline silicon region has a diameter of from about 14.75 to about 15.25 mm and a length of from about 90 to about 120 mm. The freeze-out melt region typically has a diameter of from about 10 to about 20 mm, more typically about 10 mm. It is to be appreciated that although the above ranges represent typical dimensions of the zoned and annealed silicon core, other ranges are also possible depending on the specific float-zone crystal-growth apparatus used. Typically, the zoned and annealed silicon core further includes a tang end region disposed adjacent the freeze-out melt region, opposite the single crystalline silicon region. The tang end region includes polycrystalline silicon that remains from the polycrystalline silicon core and that has not been zoned. Although the tang end region need not be present in the zoned silicon core, the tang end region may be used to mount the zoned silicon core on a cutting device or zoning machine.

The zoned silicon core is annealed at a temperature of at least 1150° C., typically from 1150° C. to 1360° C., for a period of at least 2 hours in an oven. The annealing reduces internal stress within the zoned silicon core and permits acceptable results from the determination of carbon concentration in the section provided from the zoned and annealed silicon core. As described above, for purposes of the present invention, the important feature is that the section of the zoned and annealed silicon core is provided regardless of the origin of the section or the methods used to provide the section. As such, it is to be appreciated that the present invention may be practiced by providing the section from the zoned and annealed silicon core that is formed by a third party.

As set forth above, the section is provided from the zoned and annealed silicon core. More specifically, the section is provided from the freeze-out melt region of the zoned and annealed silicon core with the entire freeze-out melt region in the section. The section is typically a cross section of the freeze-out melt region; however, it is to be appreciated that it may be possible for the section to be a portion of a cross section while still providing useful results based on the determination of carbon concentration in the section. The section may have a thickness of from about 3.5 to about 5.0 mm, typically from about 4.12 to about 4.17 mm, which is sufficient to include the entire freeze-out melt region. The freeze-out melt region typically has a thickness of from 3.0 to 3.4 mm.

Typically, the section is provided perpendicular to the length of the columnar shape of the zoned and annealed silicon core in order to include the entire freeze-out melt region in the section. By providing the section from the freeze-out melt region, determination of carbon concentration in the crystalline silicon is enabled with a sensitivity at less than or equal to 10 parts per billion atomic. The determination of carbon concentration in the crystalline silicon with the sensitivity at less than or equal to 10 parts per billion atomic is due primarily to higher carbon concentration in the freeze-out melt region, as compared to carbon concentration in the polycrystalline silicon composition. As a result, immeasurable differences in carbon concentration in polycrystalline silicon compositions are magnified and thus measurable between the freeze-out melt regions, thereby enabling the sensitivity at less than or equal to 10 parts per billion atomic in the determination of carbon concentration in the crystalline silicon.

The section is removed from the freeze-out melt region of the zone and annealed silicon core using any method known in the art. For example, the section is typically removed by cutting the section from the freeze-out melt region using a cutting device. The cutting device may be a saw, a water jet, a laser beam, etc. Typically, the cutting device is a precision saw having a diamond-tipped blade with an ability to securely mount the zoned and annealed silicon cores, such as a Struer saw. To remove the section from the freeze-out melt region, the zoned and annealed silicon core may be mounted on the cutting device at the tang end region of the zoned and annealed silicon core with a chuck mount. Prior to mounting the zoned and annealed silicon core, a portion of the tang end region may be removed from the zoned and annealed silicon core in order to fit the zoned and annealed silicon core in the cutting device and to properly orient the zoned and annealed silicon core in preparation for removing the section. The portion of the tang end region may be removed at a distance of from about 10 to about 15 mm from the freeze-out melt region.

The zoned and annealed silicon core may be positioned with a template to orient a cutting position for the cutting device. More specifically, the template may be included on the Struer saw to measure out and indicate an exact cutting location. A right edge of the plastic template may be aligned against the chuck mount. A center of the freeze-out melt region may be aligned with a left edge of the plastic template. The section is then cut from the freeze-out melt region. The Struer saw is then used, with the zoned and annealed silicon core position as described, to cut the section from the freeze-out melt region with the entire freeze-out melt region included in the section.

After removing the section from the freeze-out melt region, the section may be polished in order to prepare a surface of the section for determination of carbon concentration. The section is typically mounted on a glass plate and may be polished for at least 10 minutes with quartz wax. A combination of polishing oil commercially available from Speedfam-IPEC, Inc. of Chandler, Ariz. and 1 micron Metadi® II diamond paste, commercially available from Buehler Ltd. of Lake Bluff, Ill., may be used to polish the section. The section may then be degreased with an organic solvent. A final thickness of the section is typically about 4.00 mm±0.05.

Carbon concentration of the section is then determined through methods known in the art. Typically, the carbon concentration of the section is determined with a Fourier Transform infrared (FT-IR) spectrometer. The method of determining carbon concentration in the section with the FT-IR spectrometer is substantially the same as the method described in ASTM F 1391-93 in terms of calibrating the spectrometer and determining the carbon concentration of the section; however, the section used for purposes of the present invention is different from the section described in ASTM F 1391-93 in terms of thickness of the section.

Optionally, the carbon concentration of the single crystalline silicon region may be determined based on the carbon concentration of the section, the weight of the section, the weight of the single crystalline silicon region, and an effective segregation coefficient. More specifically, the carbon concentration of the single crystalline silicon region may be represented by the following equation:

$$C_{SCS} = \frac{C_S \times W_S}{W_{SCS} \times E}$$

wherein $C_{scs}$ is carbon concentration in the single crystalline silicon region, $C_s$ is the carbon concentration in the section, as determined through the method as set forth above, $W_s$ is a weight of the section, $W_{scs}$ is a weight of the single crystalline silicon section, and E is an effective segregation coefficient.

The weight of the section is determined after polishing and degreasing the section, and may be determined prior to, during, or after determining the carbon concentration in the section. The weight of the single crystalline silicon section is typically determined after the section is removed from the zoned and annealed silicon core. More specifically, the single crystalline silicon region may be cut from the freeze-out melt region, after which the weight of the single crystalline silicon region may be determined.

The effective segregation coefficient is a constant that correlates the carbon concentration in the freeze-out melt region to a carbon concentration in the polycrystalline silicon composition. The effective segregation coefficient may be predetermined for the polycrystalline silicon composition, in general, and may further be predetermined for a given float-zone crystal-growth apparatus and conditions under which the polycrystalline silicon core is zoned. Alternatively, the method of the present invention may further include the step of determining the effective segregation coefficient.

As set forth above, the carbon concentration in the freeze-out melt region is higher than the carbon concentration in the polycrystalline silicon composition. The relationship between the carbon concentration in the freeze-out melt region and the polycrystalline silicon composition may be directly correlated, as represented by the effective segregation coefficient, by determining the carbon concentration in the freeze-out melt region and the carbon concentration in a reference polycrystalline silicon core of known carbon concentration. Typically, the effective segregation coefficient is determined with a series of reference polycrystalline silicon cores having different carbon concentrations.

The zoned and annealed silicon reference cores are zoned and annealed under the same conditions as the zoned and annealed silicon core. Further, the zoned and annealed silicon reference cores have a substantially similar columnar shape and include the same regions as the zoned and annealed silicon core.

A reference section may be provided from the reference polycrystalline silicon composition, typically from the tang end region of the zoned and annealed silicon reference core or cores. More specifically, the reference section is typically removed from the tang end region of the reference core perpendicular to the columnar shape, preferably at a location immediately after the freeze-out melt region. A second reference section is removed from the freeze-out melt region of the reference core perpendicular to the length of the columnar shape with the entire freeze-out melt region in the second reference section in the same manner as described above. The carbon concentration of the reference section and the second reference section is determined with a Fourier Transform infrared spectrometer.

Carbon concentrations from reference sections and second reference sections may be plotted on X-Y coordinates, as shown in FIG. 1, with the carbon concentration of the reference section plotted on the Y axis. The carbon concentration for the corresponding second reference section is multiplied by a weight of the second reference section and divided by a weight of the single crystalline silicon region in order to adjust for differences in carbon concentration based on the length of the single crystalline silicon region, with the resulting value plotted on the X axis. The intersection between the two carbon concentrations is marked, and the same is done for additional zoned and annealed silicon reference cores of different known carbon concentration in order to generate a plot representing the relationship between the carbon concentration in the reference polycrystalline silicon composition and the adjusted carbon concentration of the freeze-out melt region. A sloped line may be fit to the plot, with an inverse of the slope of the line being the effective segregation coefficient.

Carbon concentration of the polycrystalline silicon composition may be determined based on the carbon concentration of the section. Different algorithms are used to determine carbon concentration in the polycrystalline silicon composition depending upon whether the polycrystalline silicon core is extracted perpendicular or parallel to the columnar shape of the polycrystalline silicon composition. Such algorithms are known in the art and are specifically described in ASTM F 1723-03.

EXAMPLES

Determination of Effective Segregation Coefficient

The effective segregation coefficient is determined with zoned and annealed silicon reference cores provided from reference polycrystalline silicon compositions of known carbon concentration. More specifically, reference cores are provided from reference polycrystalline silicon compositions having known carbon concentrations of 0.050, 0.80, 0.150, 0.130, 0.140, 0.160, and 0.165 ppma. The zoned and annealed silicon reference cores are first degreased and etched before zoning and annealing under conditions that are known in the art.

A reference section is provided from a tang end region of each zoned and annealed silicon reference core in order to verify the carbon concentration in the reference polycrystalline silicon composition. More specifically, the reference section is removed from the tang end region of the reference core perpendicular to the columnar shape at a location immediately after the freeze-out melt region. A second reference section is removed from the freeze-out melt region of each reference core, perpendicular to the length of the columnar shape, with the entire freeze-out melt region in the second reference section. The reference section and the second reference section are then polished to obtain a thickness of the reference section of about 2.00±0.05 mm and a thickness of the second reference section of about 4.00±0.05 mm. The carbon concentration of the reference section and the second reference section is determined with a Fourier Transform infrared spectrometer in accordance with ASTM F 1391-93. Because all of the carbon values are above 0.050 ppma, the numbers obtained from the reference section are detectable and reliable, since the existing method of determining carbon concentration in polycrystalline silicon compositions are only sensitive to carbon concentrations of 50 ppba, i.e., 0.050 ppma, or greater.

Carbon concentrations from the reference sections and second reference sections are plotted on X-Y coordinates, as shown in FIG. 1, with the carbon concentration of the reference section plotted on the Y axis. The carbon concentration for the corresponding second reference section is multiplied by a weight of the second reference section and divided by a weight of the single crystalline silicon region in order to adjust for differences in carbon concentration based on the length of the single crystalline silicon region, with the resulting value plotted on the X axis. The intersections between the respective carbon concentrations are marked, in order to generate a plot representing the relationship between the carbon concentration in the reference polycrystalline silicon composition and the adjusted carbon concentration of the freeze-out melt region. A sloped line is fit to the plot, with the effective segregation coefficient derived from the inverse of the slope of the line. In this case, the slope of the line is 2.7869, with the effective segregation coefficient being 0.3588. This effective segregation coefficient is used to determine carbon concentrations in the single crystalline silicon regions of Examples 1-34 based on carbon concentrations in the sections provided from the freeze-out melt regions.

Examples 1-34

Carbon concentrations are determined from a freeze-out melt region of zoned and annealed silicon cores obtained from different polycrystalline silicon compositions. To obtain the carbon concentrations shown in Table 1, various polycrystalline silicon compositions are provided having unknown carbon concentrations. A polycrystalline silicon core is extracted from each of the polycrystalline silicon compositions with a diamond core drill using a drill press. Each of the polycrystalline silicon cores has a diameter of about 19 mm and a length of about 110 mm. The polycrystalline silicon cores are degreased with ozone. The polycrystalline silicon cores are then placed into a clean etch boat including a solution of nitric acid and hydrofluoric acid and etched for a sufficient amount of time to remove about 100 μm from a surface of the polycrystalline silicon cores.

The polycrystalline silicon cores are then float-zoned in a float-zone crystal-growth apparatus to form zoned silicon cores. The resulting zoned silicon cores have a columnar shape and include a single crystalline silicon region, the freeze-out melt region, and a tang end region including polycrystalline silicon. The single crystalline silicon region has a diameter of from about 14.75 to about 15.25 mm and a length of from about 90 to about 120 mm. The freeze-out melt region has a diameter of about 10 mm.

The zoned silicon cores are annealed at a temperature of about 1360° C. for a period of about 2 hours in an oven. Cross sections are provided from the freeze-out melt region of the zoned and annealed silicon cores with the entire freeze-out melt region in the section. The cross sections have a thickness of from about 4.12 to about 4.17 mm, which is sufficient to include the entire freeze-out melt region. The cross section is removed by cutting the section from the freeze-out melt region using a Struer saw. To remove the section from the freeze-out melt region, the zoned and annealed silicon core is mounted on the Struer saw at the tang end region with a chuck mount. A template is included on the Struer saw to measure out and indicate an exact cutting location. The zoned and annealed silicon core is positioned with the template to orient a cutting position for the Struer saw. A right edge of the plastic template is aligned against the chuck mount. A center of the freeze-out melt region is aligned with a left edge of the plastic template. The section is then cut from the freeze-out melt region. The weight of the single crystalline silicon section is determined after the section is removed from the zoned and annealed silicon core.

The cross sections are then polished for at least 10 minutes by mounting the section on a glass plate with quartz wax. A combination of polishing oil commercially available from Speedfam-IPEC, Inc. of Chandler, Ariz. and 1 micron Metadi® II diamond paste, commercially available from Buehler Ltd. of Lake Bluff, Ill., is used to polish the section. The cross section is then degreased with an organic solvent. A final thickness of the section is about 4.00 mm±0.05. The weight of the cross section is determined after polishing and degreasing the section.

Carbon concentration of the section is then determined with a Fourier Transform infrared (FT-IR) spectrometer. The method of determining carbon concentration in the section with the FT-IR spectrometer is substantially the same as the method described in ASTM F 1391-93 in terms of calibrating the spectrometer and determining the carbon concentration of the section; however, the section used for purposes of the present invention is different from the section described in ASTM F 1391-93 in terms of thickness of the section. Referring to Table 1 below, specific examples of carbon concentration determined in accordance with the present invention are shown, wherein $C_s$ is a carbon concentration of the cross section, in parts per billion atomic, and $D_{fmr}$ is the detection limit, in parts per billion atomic, for the freeze-out melt region.

TABLE 1

| Example | $C_s$ (ppba) | $D_{fmr}$ (ppba) |
|---|---|---|
| 1 | 7 | 2 |
| 2 | 17 | 1 |
| 3 | 7 | 2 |
| 4 | 18 | 2 |
| 5 | 1 | 1 |

TABLE 1-continued

| Example | $C_s$ (ppba) | $D_{fmr}$ (ppba) |
|---|---|---|
| 6 | 7 | 2 |
| 7 | 2 | 1 |
| 8 | 31 | 4 |
| 9 | 6 | 1 |
| 10 | 22 | 2 |
| 11 | 5 | 2 |
| 12 | 16 | 11 |
| 13 | 25 | 3 |
| 14 | 29 | 2 |
| 15 | 28 | 2 |
| 16 | 24 | 2 |
| 17 | 15 | 2 |
| 18 | 22 | 1 |
| 19 | 22 | 1 |
| 20 | 16 | 1 |
| 21 | 24 | 2 |
| 22 | 43 | 3 |
| 23 | 23 | 2 |
| 24 | 23 | 2 |
| 25 | 34 | 3 |
| 26 | 24 | 2 |
| 27 | 24 | 2 |
| 28 | 22 | 1 |
| 29 | 20 | 2 |
| 30 | 41 | 3 |
| 31 | 37 | 2 |
| 32 | 20 | 1 |
| 33 | 25 | 2 |
| 34 | 21 | 3 |

Detection limits for the second reference sections, which are taken from the freeze-out melt region of the zoned and annealed silicon cores, are determined by the following equation:

$$D_{fmr} = \frac{\left(\frac{0.82 * D_{frm} * W_s}{W_{scs}}\right)}{0.3588} \times 1000$$

wherein $W_s$ is a weight of the second reference section, $W_{scs}$ is a weight of the single crystalline silicon region of the zoned and annealed silicon core, and $D_{frm}$ is a detection limit for the second reference section taken from the freeze-out melt region, in parts per million atomic, and is determined by the following equation:

$$D_{fmr} = \left(\frac{-2.0}{T_s}\right)\ln(10^{-A_s})$$

wherein $T_s$ is the thickness of the reference section and $A_s$ is the absorbance of the second reference section, with baseline noise of from 625 to 650 cm$^{-1}$, as determined with the FT-IR spectrometer.

Comparative Example 1-34

Carbon concentration of the polycrystalline silicon composition for each of the above Examples 1-34, taken from the same exact polycrystalline silicon cores used for Examples 1-34, are measured in accordance with ASTM F 1723-03 and ASTM F 1391-92. Cross sections are extracted from the tang end regions of the polycrystalline silicon cores for determination of carbon concentration. Referring to Table 2 below, specific examples of carbon concentration determined in accordance with ASTM F 1723-03 and ASTM F 1391-93 are shown, wherein $C_s$ is a carbon concentration of the cross section, in parts per billion atomic, and $D_{psc}$ is the detection limit, in parts per billion atomic, for the polycrystalline silicon composition.

TABLE 2

| Example | $C_s$ (ppba) | $D_{psc}$ (ppba) |
|---|---|---|
| 1 | 5 | 61 |
| 2 | 29 | 29 |
| 3 | 3 | 39 |
| 4 | 25 | 21 |
| 5 | 8 | 43 |
| 6 | 16 | 36 |
| 7 | 25 | 34 |
| 8 | 25 | 30 |
| 9 | 12 | 30 |
| 10 | 14 | 32 |
| 11 | 7 | 44 |
| 12 | 27 | 31 |
| 13 | 8 | 39 |
| 14 | 23 | 38 |
| 15 | 23 | 28 |
| 16 | 19 | 43 |
| 17 | 25 | 35 |
| 18 | 27 | 32 |
| 19 | 18 | 28 |
| 20 | 14 | 22 |
| 21 | 16 | 26 |
| 22 | 33 | 27 |
| 23 | 15 | 26 |
| 24 | 14 | 25 |
| 25 | 31 | 30 |
| 26 | 30 | 34 |
| 27 | 22 | 37 |
| 28 | 19 | 35 |
| 29 | 31 | 39 |
| 30 | 11 | 22 |
| 31 | 16 | 35 |
| 32 | 26 | 31 |
| 33 | 17 | 35 |
| 34 | 25 | 22 |

Detection limits for the reference sections, which are taken from the polycrystalline silicon composition, are determined by the following equation:

$$D_{psc} = \left(\frac{-2.0}{T_s}\right)\ln(10^{-A_s})$$

wherein $T_s$ is the thickness of the reference section and $A_s$ is the absorbance of the reference section, with baseline noise of from 625 to 650 cm$^{-1}$, as determined with the FT-IR spectrometer.

Results

Referring to the respective detection limits for the Examples 1-34 and the Comparative Examples 1-34, it is apparent that the detection limits, $D_{fmr}$, for the Examples 1-34 are much lower than the detection limits, $D_{psc}$, for the Comparative Examples 1-34. Specifically, an average detection limit for Examples 1-34 is 2 ppba, with a standard deviation of 2, a minimum detection limit of 1 ppba, and a maximum detection limit of 11. An average detection limit for the Comparative Examples is 33 ppba, with a standard deviation of 8, a minimum detection limit of 21, and a maximum detection limit of 61. As such, the results indicate an inherent sensitivity advantage using the method of the present invention.

The invention has been described in an illustrative manner, and it is to be appreciated that the terminology which has been used is intended to be in the nature of words of description rather than of limitation. Obviously, many modifications and variations of the present invention are possible in view of the above teachings. It is, therefore, to be appreciated that within the scope of the claims the invention may be practiced otherwise than as specifically described.

What is claimed is:

1. A method of analyzing carbon concentration in crystalline silicon, said method comprising the steps of:
providing a zoned and annealed silicon core extracted from a polycrystalline silicon composition with the zoned and annealed silicon core having a columnar shape and including a single crystalline silicon region and a freeze-out melt region with the freeze-out melt region disposed adjacent to the single crystalline silicon region and with the regions spaced along a length of the columnar shape;
removing a section from the zoned and annealed silicon core perpendicular to the length of the columnar shape;
determining carbon concentration of the section;
optionally, determining a weight of the section;
optionally, determining a weight of the single crystalline silicon region;
optionally, determining carbon concentration of the single crystalline silicon region based on the carbon concentration of the section, the weight of the section, the weight of the single crystalline silicon region, and an effective segregation coefficient;
optionally, determining carbon concentration of the polycrystalline silicon composition based on the carbon concentration of the single crystalline silicon region;
wherein the step of removing the section is further defined as removing the section from the freeze-out melt region with the entire freeze-out melt region in the section to enable determination of carbon concentration in the crystalline silicon with a sensitivity at less than or equal to 10 parts per billion atomic.

2. A method as set forth in claim 1 wherein the zoned and annealed silicon core further includes a tang end region disposed adjacent the freeze-out melt region opposite the single crystalline silicon region.

3. A method as set forth in claim 2 further comprising the step of mounting the zoned and annealed silicon core on a cutting device at the tang end region of the zoned and annealed silicon core.

4. A method as set forth in claim 3 wherein the step of removing the section further comprises the step of positioning the zoned and annealed silicon core with a template to orient a cutting position for the cutting device.

5. A method as set forth in claim 1 further comprising the step of polishing the section prior to the step of determining the weight of the section and prior to the step of determining the carbon concentration of the section.

6. A method as set forth in claim 1 further comprising the step of degreasing the section prior to the step of determining the weight of the section and prior to the step of determining the carbon concentration of the section.

7. A method as set forth in claim 1 further comprising the step of providing a zoned and annealed silicon reference core from a reference polycrystalline silicon composition of known carbon concentration that is zoned and annealed under the same conditions as the zoned and annealed silicon core and that has a substantially similar columnar shape and includes the same regions as the zoned and annealed silicon core with a single crystalline silicon region of the reference core having substantially the same length as a length of the single crystalline silicon region of the zoned and annealed silicon core.

8. A method as set forth in claim 7 further comprising the step of providing a reference section from the reference polycrystalline silicon composition.

9. A method as set forth in claim 8 further comprising the step of removing a second reference section from the freeze-out melt region of the reference core perpendicular to the length of the columnar shape with the entire freeze-out melt region in the second reference section.

10. A method as set forth in claim 9 further comprising the step of determining the carbon concentration of the reference section and the second reference section with a Fourier Transform infrared spectrometer.

11. A method as set forth in claim 10 further comprising the step of determining the effective segregation coefficient based on the differences in carbon concentration between the reference section and the second reference section.

12. A method as set forth in claim 1 further comprising the step of annealing a zoned silicon core extracted from the crystalline silicon composition.

13. A method as set forth in claim 12 further comprising the step of zoning a polycrystalline silicon core extracted from the crystalline silicon composition.

14. A method as set forth in claim 13 further comprising the step of etching the polycrystalline silicon core in acid.

15. A method as set forth in claim 14 further comprising the step of extracting the polycrystalline silicon core from a polycrystalline silicon composition.

16. A method of analyzing carbon concentration in crystalline silicon, said method comprising the steps of:
    providing a section from a zoned and annealed silicon core extracted from a polycrystalline silicon composition and having a columnar shape and including a single crystalline silicon region and a freeze-out melt region with the freeze-out melt region disposed adjacent to the single crystalline silicon region and with the regions spaced along a length of the columnar shape;
    determining carbon concentration of the section;
    optionally, determining a weight of the section;
    optionally, determining carbon concentration of the single crystalline silicon region based on the carbon concentration of the section, the weight of the section, a weight of the single crystalline silicon region, and an effective segregation coefficient;
    optionally, determining carbon concentration of the polycrystalline silicon composition based on the carbon concentration of the single crystalline silicon region;
    wherein the step of providing the section is further defined as providing the section from the freeze-out melt region with the entire freeze-out melt region in the section to enable determination of carbon concentration in the crystalline silicon with a sensitivity at less than or equal to 10 parts per billion atomic.

17. A method as set forth in claim 16 further comprising the step of polishing the section prior to the step of determining the weight of the section and prior to the step of determining the carbon concentration of the section.

18. A method as set forth in claim 16 further comprising the step of degreasing the section prior to the step of determining the weight of the section and prior to the step of determining the carbon concentration of the section.

19. A method as set forth in claim 16 further comprising the step of providing a reference section from a reference polycrystalline silicon composition of known carbon concentration.

20. A method as set forth in claim 19 further comprising the step of providing a second reference section from a freeze-out melt region of a zoned and annealed silicon reference core from a reference polycrystalline silicon composition of known carbon concentration that is zoned and annealed under the same conditions as the zoned and annealed silicon core and that has a substantially similar columnar shape and includes the same regions as the zoned and annealed silicon core with the single crystalline silicon region of the reference core having substantially the same length as a length of the single crystalline silicon region of the zoned and annealed silicon core with the entire freeze-out melt region in the second reference section.

21. A method as set forth in claim 20 further comprising the step of determining the carbon concentration of the reference section and the second reference section with a Fourier Transform infrared spectrometer.

22. A method as set forth in claim 21 further comprising the step of determining the effective segregation coefficient based on the differences in carbon concentration between the reference section and the second reference section.

23. A method comprising the step of:
    removing a section from a zoned and annealed silicon core having a columnar shape and including a single crystalline silicon region and a freeze-out melt region with the freeze-out melt region disposed adjacent to the single crystalline silicon region and with the regions spaced along a length of the columnar shape,
    wherein the section is removed from the zoned and annealed silicon core perpendicular to the length of the columnar shape and from the freeze-out melt region with the entire freeze-out melt region in the section.

24. A method as set forth in claim 23 wherein the zoned and annealed silicon core further includes a tang end region disposed adjacent the freeze-out melt region opposite the single crystalline silicon region.

25. A method as set forth in claim 24 wherein step of removing the section further comprises the step of mounting the zoned and annealed silicon core on a cutting device at the tang end region of the zoned and annealed silicon core.

26. A method as set forth in claim 25 wherein the step of removing the section further comprises the step of positioning the zoned and annealed silicon core with a template to orient a cutting position for the cutting device.

* * * * *